United States Patent [19]

Ferris

[11] Patent Number: 4,808,705

[45] Date of Patent: Feb. 28, 1989

[54] STABLE FORMULATIONS OF RICIN TOXIN A CHAIN AND OF RTA-IMMUNOCONJUGATES AND STABILIZER SCREENING METHODS THEREFOR

[75] Inventor: Robert Ferris, Walnut Creek, Calif.

[73] Assignee: Cetus Corporation, Emeryville, Calif.

[21] Appl. No.: 944,347

[22] Filed: Dec. 19, 1986

[51] Int. Cl.$^4$ ............... C07K 15/00; A61K 39/395
[52] U.S. Cl. .................................. 530/391; 530/390; 530/808; 530/370; 424/85.91; 514/2; 514/885; 514/8
[58] Field of Search ............. 424/85; 530/391; 514/2, 514/8

[56] References Cited

U.S. PATENT DOCUMENTS 4,439,181  3/1984  Blackshear et al. ............. 604/56
4,507,234  3/1985  Kato et al. ......................... 530/363
4,623,717  11/1986 Fernandes et al. ................ 530/380

OTHER PUBLICATIONS

Jansen et al., *Immunological Rev.*, vol. 62, 1982, pp. 185-216.

Primary Examiner—Delbert R. Phillips
Assistant Examiner—Garnette D. Draper
Attorney, Agent, or Firm—Leona L. Lauder; Albert P. Halluin; Gregory J. Giotta

[57] ABSTRACT

Highly stable pharmaceutical compositions suitable for parenteral administration to animals or humans comprising a therapeutically effective amount of an RTA-immunoconjugate dissolved in an inert carrier method comprising a stabilizer are claimed. Screening methods for selecting stabilizers effective in preventing precipitation and aggregation of such compositions are described. Preferred stabilizers includes glycerol at a concentration (v/v) of from about 25 to about 35%; dextran sulfates having molecular weights from about $0.1 \times 10^6$ to about $2 \times 10^6$ daltons; and human serum albumin.

The invention further comprises such compositions which have been lyophilized and/or reconstituted wherein the stabilizer is non-volatile, and may further comprise a carbohydrate stabilizer.

The invention further comprises stabilized RTA compositions.

46 Claims, 6 Drawing Sheets

STABLE FORMULATIONS OF RICIN TOXIN A CHAIN AND OF RTA-IMMUNOCONJUGATES AND STABILIZER SCREENING METHODS THEREFOR

FIELD OF THE INVENTION

This invention is in the field of biochemical engineering. More particularly, this invention concerns formulations of ricin toxin A chain (RTA) and pharmaceutical compositions of ricin toxin A chain immunoconjugates. Further, the invention concerns screening processes for finding stabilizers for ricin toxin A chain and RTA-immunoconjugate preparations.

BACKGROUND OF THE INVENTION

Ricin toxin is a naturally occurring toxin that is derived from the seeds of *Ricinus communis*, commonly known as castor beans. It is composed of an enzymatically active cytotoxic polypeptide chain, commonly called the "A" chain and referred to herein as "RTA", that is bound by a single disulfide link to a second polypeptide chain commonly called the "B" chain that is presumed to be responsible for binding the toxin molecule to cells and aiding in translocating RTA into the cytoplasm. RTA is capable of catalytically inactivating the large subunit of ribosomes in vitro and the mechanism of RTA for in vivo cytotoxicity is believed to reside in this capacity for ribosome inactivation.

Olsnes, S. *Perspectives in Toxicology*, A. W. Bernheimer, Ed (1977) J. Wiley & Sons, NY, pp 122–147 and Olsnes, S., et al, *Molecular Action of Toxins and Viruses*, Cohen et al., Ed (1982) Elsevier, Amsterdam, pp 51–105 characterize native RTA as having an apparent molecular weight of 32,000. Copending, commonly owned U.S. patent application Ser. No. 715,934 filed Mar. 25, 1985 and a continuation-in-part thereof, Ser. No. 837,583 filed Mar. 7, 1986, disclose the native structural gene for RTA, the deduced amino acid sequence of RTA, DNA constructs for cloning and expressing the RTA gene, and transformed bacteria capable of synthesizing intracellularly produced, soluble recombinant RTA (srRTA). Those patent applications further describe the production of such recombinant RTA by such bacteria and a procedure for recovering RTA from the bacteria.

Copending, commonly owned U.S. patent application Ser. No. 905,283, filed Sept. 9, 1986, describes a method for recovering substantially pure, soluble recombinant RTA (srRTA) in high yields from microorganisms transformed to express RTA.

Copending, commonly owned U.S. patent application Ser. No. 806,256 filed Dec. 6, 1985, and a continuation-in-part thereof, U.S. Ser. No. 913,357 filed Sept. 30, 1986, disclose immunoconjugates comprising murine monoclonal antibodies conjugated to RTA which are effective against human ovarian tumors.

Copending, commonly owned U.S. patent application Ser. No. 690,750 filed Jan. 11, 1985 and a continuation-in-part thereof, U.S. Ser. No. 842,476 filed Mar. 21, 1986, disclose immunoconjugates comprising murine monoclonal antibodies conjugated to RTA which are effective against human breast tumors.

Native RTA high purified by affinity chromatography is available from SIGMA chemical company in a 40% glycerol solution at pH 6.0 containing 10 mM phosphate, 0.15 M NaCl, 10 mM galactose and 0.5 mM dithioerythritol.

RTA subunits of the ricin toxin whether native or recombinant, when not attached to the ricin toxin B chain (RTB) subunit, are hydrophobic. In formulations containing water, the RTA subunits tend to adhere to each other and aggregate at the water/air interface and around air bubbles. The stability problems associated with RTA also affect RTA-immunoconjugate preparations. The instant invention provides solutions to such stability problems.

SUMMARY OF THE INVENTION

The instant invention provides methods of screening for compounds that stabilize RTA in solution, and are therefore considered to be suitable candidate stabilizers for RTA-immunoconjugate preparations. The screening methods comprise a thermal stability assay wherein RTA and the candidate stabilizer are mixed and heated to an elevated temperature and maintained at such temperature for a set interval during which absorbance readings are periodically taken to check for precipitation and aggregation. The absorbance readings are then compared to a standard curve. The screening processes can also comprise an agitation step.

Preferred stabilizers include the following: glycerol in a volume to volume (v/v) concentration of from about 25 to 35%, most preferably about 30%; dextran sulfates having molecular weights of from about $0.1 \times 10^6$ to about $2 \times 10^6$ daltons, preferably from about $0.3 \times 10^6$ to about $1 \times 10^6$ daltons, and most preferably about $0.5 \times 10^6$ daltons; and human serum albumin. Most preferably the dextran sulfates are in a weight to volume (w/v) concentration of from about 0.002 to about 2%, preferably from 0.006 to 1.5%, and more preferably 0.01 to 1%. Human serum albumin is preferably in a weight to volume (w/v) concentration of from about 1 to about 5%, preferably 2 to 4%, more preferably 2.5 to 3.5%, and most preferably about 3%.

One aspect of the instant invention concerns highly stable compositions comprising RTA dissolved in an inert carrier medium comprising a stabilizer selected by the screening processes described herein.

The invention further provides for highly stable pharmaceutical compositions suitable for parenteral administration comprising a therapeutically effective amount of an RTA-immunoconjugate dissolved in an inert carrier medium comprising a stabilizer selected by the screening process described herein.

The invention further concerns lyophilized pharmaceutical compositions of such RTA-immunoconjugates which when re-solubilized are biologically active, stable formulations which are resistant to precipitation and aggregation upon agitation. Such lyophilized pharmaceutical compositions may also contain a carbohydrate stabilizer, preferably, maltose or sucrose, most preferably sucrose. When maltose is the carbohydrate stabilizer for such lyophilized preparations, it is in a concentration range (w/v) from about 0.5 to about 20%, preferably 0.75 to 5%, and more preferably 1 to 2%; whereas when sucrose is the carbohydrate stabilizer, it is in a concentration range (w/v) of from about 0.5 to about 10%, preferably from 0.75 to 5%, and more preferably from 1 to 2%. Said lyophilized formulations are further characterized by the ease at which they are resolubilized.

The pH of such compositions is from about 6.5 to about 8, preferably from about 6.8 to about 7.8, and more preferably from about 7.1 to 7.2.

DETAILED DESCRIPTION

The instant invention solves the problems of precipitation and aggregation of RTA and RTA-immunoconjugate preparations.

The terms "ricin A", "ricin toxin A" and "RTA" refer to a protein, whether native or recombinantly produced, whose amino acid sequence is the same or substantially similar to that of the ricin A peptide which is extractable from castor bean seeds. The ricin A of castor beans is approximately 265 amino acids in length and has a molecular weight of approximately 32,000 daltons. However, it is known that the precise sequence varies depending on the variety of bean, and, indeed, that at least two slightly different forms of ricin A may be present in a single variety.

"Substantially similar" means that the protein in question must be approximately the same length (arbitrarily within around 10%, although it is known that the essential features for activity may reside in a peptide of shorter length—i.e., a "fragment", or of longer sequence—i.e., a fusion protein) but, more importantly, and critical to the definition, must retain the capacity of ricin A chain to interact with, and incapacitate, the 60S ribosome subunit. Alterations in chain length which do not greatly impair this enzymatic activity are included. It is well known that some small alterations in protein sequence may be possible without disturbing the functional abilities of the protein molecule, although other modifications are totally destructive. It is not currently possible to predict with any assurance into which category a particular alteration will fall. The definition herein permits any modifications which are in the first category. Such alterations could result from chance mutuations in the gene sequence or from deliberate alterations thereof. In summary, modified forms of amino acid sequence which retain the enzymatic activity of ricin A are included.

Further, as is well known, protein sequences may be modified by post-translational processing such as association with other molecules, for example, glycosides, lipids, or such inorganic ions as phosphate. The ionization status will also vary depending on the pH of the medium or the pH at which crystallization or precipitation of the isolated form occurs. Further, the presence of air may cause oxidation of labile groups, such as —SH. Included within the definition of ricin A are all such modifications of a particular primary structure—i.e., e.g., both glycosylated and non-glycosylated forms, neutral forms, acidic and basic salts, lipid or other associated peptide forms, side chain alterations due to oxidation or derivatization, and any other such modifications of an amino acid sequence which would be encoded by the same genetic codon sequence.

As used herein, "soluble" refers to a protein which remains in the supernatant after centrifugation for 30 min at $100,000 \times$ g in aqueous buffer under physiologically isotonic conditions, for example, 0.14 M sodium chloride or sucrose, at a protein concentration of as much as 10 mg/ml. These conditions specifically relate to the absence of detergents or other denaturants in effective concentrations such as guanidine or urea.

The soluble recombinant RTA (srRTA) referred to herein was produced and recovered by methods described in detail in copending, commonly owned U.S. patent application Ser. Nos. 715,934 (filed Mar. 25, 1985), 837,583 (filed Mar. 7, 1986), and 905,283 (filed Sept. 9, 1986). Said U.S. patent applications are herein incorporated by reference. As described in U.S. Ser. No. 837,583, using constructs employing codons for the leader sequence of a bacterial secreted protein, soluble biologically active ricin A chain and ricin precursor are directly obtained using procaryotic hosts, without need for further treatment to refold or solubilize the heterologous protein. Soluble recombinant ricin A may be extracted from appropriate host cells using normal mechanical disruption and may then be purified without requiring detergents or chaotropic agents.

Immunotoxins are conjugates of a monoclonal antibody and a cytotoxic agent. RTA-immunoconjugates are herein defined as an immunotoxin wherein RTA is the cytotoxic moiety. Conjugates of a monoclonal antibody and RTA may be made using a variety of bifunctional protein coupling agents. Examples of such reagents are N-succinimidyl-3-(2-pyridyldithio) propionate (SPDP), 2-iminothiolane (IT), bifunctional derivatives of imidoesters such as dimethyl adipimidate . HCl, active esters such as discussinimidyl suberate, aldehydes such as glutaraldehyde, bis-azido compounds such as bis(p-diazoniumbenzoylz)-ethylenediamine, diisocyanates such as tolylene 2,6-diisocyanate, and bis-active fluorine compounds such as 1,5-difluoro-2,4-dinitrobenzene.

The monoclonal antibodies employed in the RTA-immunoconjugates can be from any immunoglobulin class or sub-class. Preferably, the monoclonal antibodies of the RTA-immunoconjugates of this invention are in the IgG class, preferably in the IgG1, IgG2 and IgG3 subclasses, more preferably IgG1 or IgG2, and most preferably IgG1.

Recombinantly produced ricin toxin A chain (rRTA) may be produced in accordance with the methods disclosed in copending, commonly owned U.S. patent application Ser. Nos. 715,934 and 653,515, which are herein incorporated by reference.

The preparation of RTA-immunoconjugates are described in co-pending, commonly owned U.S. patent application Ser. Nos. 690,750; 806,256; 842,476 and 913,357, which are also herein incorporated by reference.

As used herein, the term "monoclonal antibody" means an antibody composition having a homogeneous antibody population. It is not intended to be limited as regards the source of the antibody or the manner in which it is made.

"Biologically active" refers to retaining the enzymatic or other biological behavior which typifies the function of the protein in its native state. The biological activity of ricin A refers in one aspect to enzymatic activity, i.e., its ability to inhibit protein synthesis in a rabbit reticulocyte in vitro translation system (a commercially available system obtainable, e.g., from Bethesda Research Laboratories, Rockville, MD). In addition to being enzymatically active, soluble preparations of ricin A toxin are also capable of exhibiting specific cytotoxic activity when conjugated with specific binding portions, for example, immunoglobulins, to form immunotoxins.

"Cytotoxic activity" refers to the specific ability of these immunotoxins to cause the destruction of cells against which they are targeted, as opposed to being generally toxic to an organism. Cytotoxic activity may be demonstrated both in vitro using cell cultures comprising the target cells or in vivo using implants or naturally occurring groups of targeted cell types. In summary, the biological activity of ricin A may be demonstrated in accordance with at least three criteria: enzymatic activity in inhibiting protein synthesis, in vitro catotoxic activity when cultured cells containing antigens specific to an immunoglobulin binding entity conjugated to the toxin are selectively killed by these immunoconjugates, and in vivo cytotoxicity wherein immunotoxins are capable of binding to and selectively killing cells reactive with the antibody which forms the binding moiety in the immunoconjugate. It is recognized that some or all of these biological activities may be absent even when immunological cross reactivity with antibodies raised against the specified protein remains.

When an RTA-immunoconjugate is used in vivo for therapy, the immunotoxin is administered to the patient in therapeutically effective amounts, that is, in amounts sufficient to eliminate, reduce or retard the increase of a patient's tumor burden. The immunotoxin is normally administered parenterally, either intraperitoneally (IP) or intravenously (IV).

For parenteral administration, the immunotoxin is formulated in unit dosage injectable form (solution, suspension, emulsion) in association with a pharmaceutically acceptable parenteral vehicle. Such vehicles are inert carrier media such as water, saline, and Ringer's solution, which are inherently nontoxic and nontherapeutic. Such carrier media comprise, in the pharmaceutical compositions of the instant invention, a stabilizer selected according to the screening processes defined herein. Such stabilizers prevent aggregation and precipitation of the RTA-immunoconjugates. The pharmaceutical compositions of this invention may also contain small amounts of additives such as substances that enhance isotonicity and chemical stability, for example, buffers and preservatives. Phosphate buffered salt solutions are preferred buffers at a concentration from about 0.05 to about 0.25 M, more preferably at or about 0.1 M. Phosphate buffered saline is a more preferred buffer at a concentration from about 0.13 to about 0.18 M, preferably at or about 0.15 M. Sodium phosphate is another preferred inert carrier medium, preferably at the same molarity range as indicated for PBS.

The concentration of the RTA-immunoconjugates in the pharmaceutical compositions of this invention are preferably from about 0.002 mg/ml to about 20 mg/ml, more preferably from about 0.01 to 10 mg/ml, still more preferably from about 0.05 to 4 mg/ml, and most preferably about 2 mg/ml. Clinicians may dilute such compositions for therapeutic administration as required.

THERMAL STABILITY ASSAY SCREENING METHOD

A heat denaturation assay was developed to screen a large number of reagents for their ability to stabilize RTA and RTA-immunoconjugates. The assay was premised on the concept that the highly hydrophobic nature of the RTA chain when disattached from the RTB chain was a major source of instability of RTA-immunoconjugate preparations. Therefore, reagents that stabilize RTA were considered to be good candidates for stabilizing RTA-immunoconjugate formulations.

RTA is particularly unstable at elevated temperatures. It was observed that 25% of srRTA at a concentration of 0.34 mg/ml precipitates from a 0.1 M sodium phosphate solution at pH 8 when maintained at 40° C. for a thirty-minute period. Given said rate of precipitation of such a srRTA standard preparation, a comparison of spectrophotometric absorbance readings of said standard with absorbance readings for a srRTA preparation at the same concentration with a candidate stabilizer also maintained at 40° C. over a thirty-minute period in the same or similar inert carrier medium indicate the effectiveness of the candidate stabilizer in preventing precipitation and aggregation of the srRTA.

Said absorbance readings are taken periodically over the thirty-minute period, preferably at one-minute intervals. Comparisons can be made between absorbance readings of RTA preparations with various concentrations of the candidate stabilizer to optimize the effective concentration thereof. The screening method can further comprise an agitation step which increases the probability of precipitation and aggregation of the srRTA subunits.

Candidate stabilizer compounds can be selected from any reagent class, but preferably from compound classes known to be therapeutically compatible, that is, for example, nontoxic and nonimmunogenic. Wang et al., *J. Parenteral Drug Assoc.*, 34:452–462 (1980) provides a review of excipients for parenteral products used in the United States.

Ones of ordinary skill in the art realize that the parameters employed in such a screening assay, that is, a 40° C. temperature, a 30-minute time period, pH 8, the use of srRTA, sodium phosphate or PBS at 0.1 M, concentrations employed, are not sacrosanct and only provide standard conditions for comparative purposes. Other conditions and the use of native or rRTA other than srRTA are encompassed within the scope of said screening method which can be defined as follows.

A method of screening for effective stabilizers for RTA and RTA-immunoconjugate preparations which comprises the steps of:

(a) establishing a standard absorbance curve for an RTA concentration in an inert carrier medium at an elevated temperature over a particular time period;

(b) selecting a candidate stabilizer compound and adding a particular concentration thereof to an RTA preparation wherein the RTA is at the same, or essentially the same, concentration in the same or similar inert carrier medium as the RTA preparation tested in step (a);

(c) subjecting the candidate stabilizer/RTA preparation of step (b) to the same, or essentially the same, testing conditions used in step (a) taking absorbance readings in the same absorbance range and at the same time intervals as used to establish the absorbance curve in step (a), and establishing an absorbance curve from said readings; and (d) comparing the absorbance curve of step (a) and that of step (c) to determine the effectiveness of the candidate stabilizer in preventing aggregation and precipitation of the RTA.

Further, said screening method can be defined as including in the testing conditions of step (a) a particular agitation protocol. Such agitation protocol would comprise, for example, inverting and uprighting the container holding the test or standard preparation a certain number of times or vortexing the container holding each test or standard preparation at a specific rate for a specific time.

STABILIZED RTA COMPOSITIONS

Therefore, by screening reagents according to the above-described thermal stability assay, stabilizers are found for compositions of RTA. Such stabilized compositions of matter comprise a biologically active amount of RTA dissolved in an inert carrier medium comprising a stabilizer selected by the above-described thermal stability assay screening method. The RTA in such compositions is preferably srRTA in a concentration of from about 0.2 to about 0.4 mg/ml, preferably about 0.34 mg/ml.

As indicated above, preferred stabilizers for such RTA preparations are glycerol, dextran sulfates (with molecular weights from about $0.1\times10^6$ to about $2\times10^6$ daltons) and human serum albumin. Preferably, the inert carrier media are PBS or sodium phosphate and water. Preferable concentrations for such stabilizers and inert carrier media are also indicated above, as well as, the preferred pH ranges for such preparations. Further, FIGS. 1 through 3 delineate the preferred concentrations of stabilizers for such preferred srRTA compositions.

FIGS. 1(A)–(B) indicate that concentrations of 10% to 50% glycerol stabilize such compositions.

FIGS. 2(A)–(B) indicate that dextran sulfate ($0.5\times10^6$ daltons) stabilizes such compositions in a range of from at least about 0.006 to at least about 1%.

FIGS. 3(A)–(B) indicates that HSA from at least about 1 to at least about 5% stabilize such formulations.

Such percentage ranges for stabilizers that are geared to stabilizing RTA at the elevated temperatures of 40° C. Other concentration ranges extrapolated therefrom that would be obvious to those of ordinary skill in the art for other temperature ranges, as at room temperature, are encompassed by the scope of this invention.

STABILIZED RTA-IMMUNOCONJUGATE PREPARATIONS--LIQUID AND LYOPHILIZED

Candidate stabilizers that effectively prevent precipitation and aggregation of RTA preparations are then tested as stabilizers for RTA-immunoconjugate preparations. Ability to prevent such precipitation and aggregated is determined by clarity of the pharmaceutical RTA-immunoconjugate compositions upon resuspension and after agitation. Such clarity determinations can be made visually or by spectrophotometric absorbance readings.

Preferred stabilizers of the instant invention for RTA-immunoconjugate preparations include glycerol in a volume to volume (v/v) concentration of from about 25 to about 35%, most preferably at or about 30%; dextran sulfates having molecular weights of from about $0.1\times10^6$ to about $2\times10^6$ daltons, preferably from about 0.3 x $10^6$ about $0.1\times10^6$ daltons, and most preferably about $0.5\times10^6$ daltons; and human serum albumin. Most preferably, such dextran sulfates are in a weight to volume (w/v) concentration in such preparations from about 0.002 to about 2%, preferably from 0.006 to 1.5%, and more preferably from 0.01 to 1%. Human serum albumin is preferably employed as a stabilizer for RTA-immunoconjugates in a weight to volume (w/v) concentration of from about 1% to about 5%, preferably 2 to 4%, more preferably about 2.5 to 3.5%, and most preferably about 3%.

Preferred carrier media are indicated above, and are most preferably PBS and sodium phosphate in water-for-injection (WFI) at the above-indicated molarities.

It is also an object of this invention to develop solid or lyophilized RTA-immunoconjugate pharmaceutical compositions which, are easily re-solubilized and which, upon re-solubilization for therapeutic administration, are biologically active and highly stable.

Such stability is not only determined by clarity of the reconstituted preparations, but importantly, that such preparations are resistant to aggregation and precipitation upon agitation.

Non-volatile stabilizers of this invention that effectively prevent aggregation and precipitation of liquid RTA and RTA-immunoconjugate preparations according to the procedures outlined above are considered good candidates for stabilizing lyophilized RTA-immunoconjugate pharmaceutical compositions. Preferred stabilizers of this invention for such lyophilized RTA-immunoconjugate compositions of this invention include dextran sulfate at the molecular weight and concentrations described above, and human serum albumin, also preferably at the concentrations described therefor above.

The stability of such lyophilized RTA-immunoconjugate pharmaceutical compositions upon reconstitution and re-solubilization, and especially upon agitation during and after re-solubilization, can be enhanced by the addition of one or more carbohydrate stabilizers, preferably one, to the compositions which are to be lyophilized. Such carbohydrate stabilizers also can improve the ease with which such lyophilized preparations are resolubilized. Preferably such carbohydrate stabilizers are selected from the group comprising glucose, sorbitol, inositol, galactitol, xylitol, mannose, mannitol, lactose, sucrose, maltose, fructose and dextrose. Further, preferred stabilizers from that group comprise sucrose, maltose, glucose, dextrose, lactose and mannitol. Still, further preferred carbohydrate stabilizers comprise sucrose, glucose, maltose and mannitol. More preferred are sucrose and maltose; and most preferred is sucrose.

When maltose is the carbohydrate stabilizer for such lyophilized preparations, it is preferably in a concentration range (w/v) of from about 0.5 to about 20%, more preferably from 0.75 to 5%, and still more preferably 1 to 2%.

When sucrose is the carbohydrate stabilizer of choice, it is preferably in a concentration range (w/v) of from about 0.5 to about 10%, preferably from 0.75 to 5%, more preferably from 1 to 2%, and most preferably about 1%.

In general, it is considered that the preferred concentration range for carbohydrate stabilizers in the lyophilized and reconstituted pharmaceutical compositions of this invention is from about 0.5 to 10%, and more preferably from about 1 to 2%.

The pH of said RTA-immunoconjugate pharmaceutical compositions is at or about physiological pH, from about 6.5 to about 8, preferably from about 6.8 to about 7.8, and more preferably from about 7.1 to 7.2

CYTOTOXICITY ASSAY

A colormetric cytotoxicity assay was used to test the biological activity of the RTA-immunoconjugates that had been lyophilized in the stabilized pharmaceutical compositions of this invention, and then reconstituted and subjected to agitation. The assay is based on the ability of various dehydrogenase enzymes in active mitochondria to cleave the tetrazolium ring in the tetrazolium salt MTT [3-(4,5-dimethylthiazoyl-2-yl)-2,5-diphenyl tetrazolium bromide] to formazan, a violet crystal. *J. Immunol. Methods,* 65:55–63, 1983. The formazan is then solubilized with an alcoho detergent solution, and read in a multi-well spectrophometer (Titertek Multiscan).

The cell line used in this assay is a breast carcinoma, MCF-7, obtained from T. Buehring at the University of California at Berkeley.

The assay takes four days to complete. Steps of the assay are outlined below on a per day basis.

Day 1

1. Each well of a 96-well tissue culture plate is filled with 50 microliters of a MEM Earles media plus 10% fetal calf serum and 1% penicillin-streptomycin at 5000 units-5000 mg/ml.

2. Twenty-five microliters of each RTA-immunoconjugate formulation test sample pre-diluted one hundred- or one thousand-fold is added to the first well of columns #2 through #11 of the 96-well plate with a maximum of ten test samples per plate. Samples are then serially diluted 1:3 to the end of each column with the remaining 25 microliters being discarded.

3. Plates are then UV sterilized for 10 min. at 100 $\mu W/CM^2$.

4. MCF-7 cell suspensions are prepared at a concentration of $1\times10^5$ cells/ml. One-hundred microliters of cell suspension is added to all wells of the 96-well plates.

5. On each plate, the #1 and #12 columns are used for the control wells. The eight wells of the #12 column are used as a maximum absorbance for the plate (this column being composed of cells and media only). The first column of each plate is used as the minimum absorbance reading for the plate, and also is used to blank the Titertek Multiscan. Each well of the first column receives 20 microliters of a 1:100 dilution of 1 mg/ml whole ricin toxin solution. At this concentration, ricin toxin will kill all of the cells in the well. (Final concentrations of 0.2 μg per well.)

6. Plates are incubated for 72 hr. at 37° C. and 6% CO2.

Day 4

1. After the 72-hr. incubation, 60 microliters of a 1:4 dilution of the stock MTT solution is added to each well of the assay plates (stock MTT solution is made up at 5 mg/ml).

2. Plates are reincubated for 4–6 hrs. at 37° C. and 5% CO2.

3. After the incubation period, all media is aspirated from each wall of the assay plates and 150 microliters of a 3% SDS-0.04 normal HCL-isopropanol mixture is added to each well. The acid-alcohol mixture solubilizes the formazan crystals and the SDS prevents precipitation of any residual serum proteins. Plates are left at room temperature for 30–60 min. to allow the plates to develop.

4. Plates are then read at 570 nm using the Titertek Multiscan plate reader.

The 50% cytotoxicity point (TCID50) for the RTA-immunoconjugate formulation test samples is then calculated. The TCID50 is the dilution at which 50% of the MCF-7 cells are killed by the RTA-immunoconjugate formulation test sample. As live cells take up the formazan dye, the lower the optical density (OD) reading, the more cells that have been killed by the test sample.

SDS-PAGE

Further, sodium dodecyl sulfate polyacrylamide gel electrophoresis (SDS-PAGE) is used to show that the RTA-immunoconjugates lyophilized in the stabilized compositions of this invention remain intact upon resuspension, reconstitution and agitation.

EXAMPLES

The following examples further illustrate the formulations and screening processes of the invention. These examples are not intended to limit the invention in any matter. In these examples all temperatures are in degrees Celsius unless otherwise indicated.

EXAMPLE 1

Thermal Stability Assays Glycerol

A 1 cm jacketed quartz cuvette was regulated at 40° C. A spectrophotometer was blanked against 980 ul of each of the glycerol concentrations tested. Said concentrations are listed in FIGS. 1 (A) and 1(B), as 10%, 20%, 30%, 40% and 50% glycerol in 0.1 M sodium phosphate at pH 8. Twenty ul of a 10 mg/ml srRTA solution in 0.1 M sodium phosphate at pH 8 was then added to the glycerol samples to a final concentration of 0.34 mg/ml.

The quartz cuvette was then inverted several times and then placed in the spectrophotometer. Absorbance readings in the UV and visible range, at 280 and 520 nm respectively, were then taken at 1 minute intervals over a thirty-minute time period. Absorbance values were then plotted as a function of time.

The graphical results are shown in FIGS. 1(A) and 1(B). It can be seen from said graphs that the glycerol concentrations substantially reduced the precipitation and aggregation of the srRTA as compared to the black circled line representing the control sample containing no stabilizer.

Dextran Sulfate

Essentially the same assay as that described immediately above for glycerol was performed with dextran sulfate ($0.5\times10^6$ daltons) as the stabilizer. However, although the control sample was the same for the glycerol tests, that is, srRTA at a 0.2 mg/ml in 0.1 M. sodium phosphate at pH 8, the dextran sulfate samples were tested in 0.15 M phosphate buffered saline at pH 7.1–7.2. The concentrations of dextran sulfate tested are listed in FIGS. 2(A)–(B) as 1%, 0.5%, 0.25%, 0.125%, 0.062%, 0.031% and 0.006%.

FIGS. 2(A) and 2(B) show the results. A srRTA sample wherein 30% glycerol is the stabilizer in 0.1 M sodium phosphate at pH 8 was also shown on the graph for comparative purposes as the black squared line. All concentrations of the dextran sulfate were shown to reduce substantially the precipitation and aggregation of the srRTA.

HSA

Figure 1A:
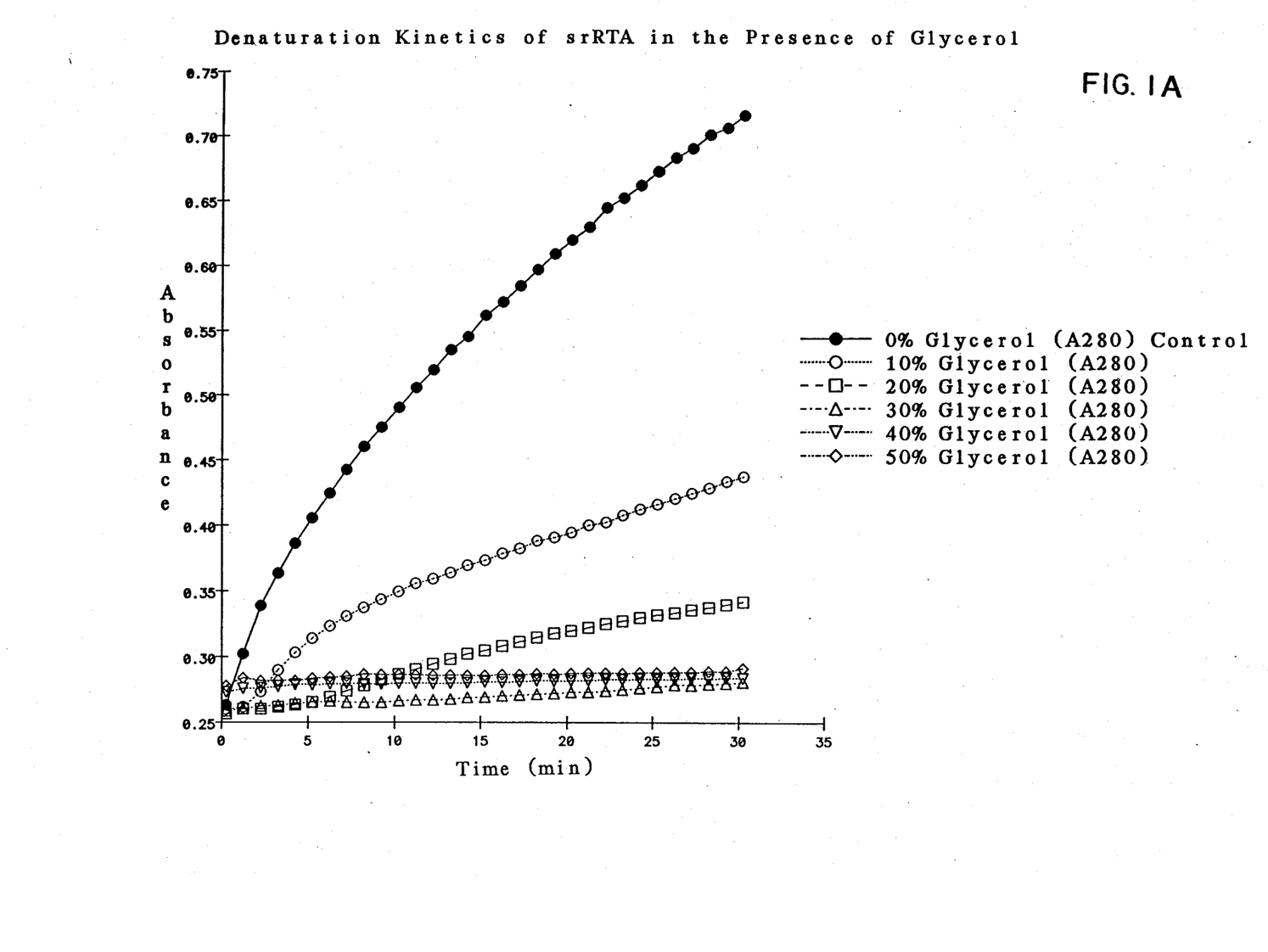
FIGS. 1(A) and (B) graphically illustrate the denaturation kinetics of recombinant soluble RTA (rsRTA) during a thermal stability assay over thirty minutes at 40° C. wherein the stabilizer is glycerol at the indicated concentrations. Such denaturation is measured by absorbance readings at A280 and A520 respectively, in FIGS. 1(A) and 1(B).
Figure 1B:
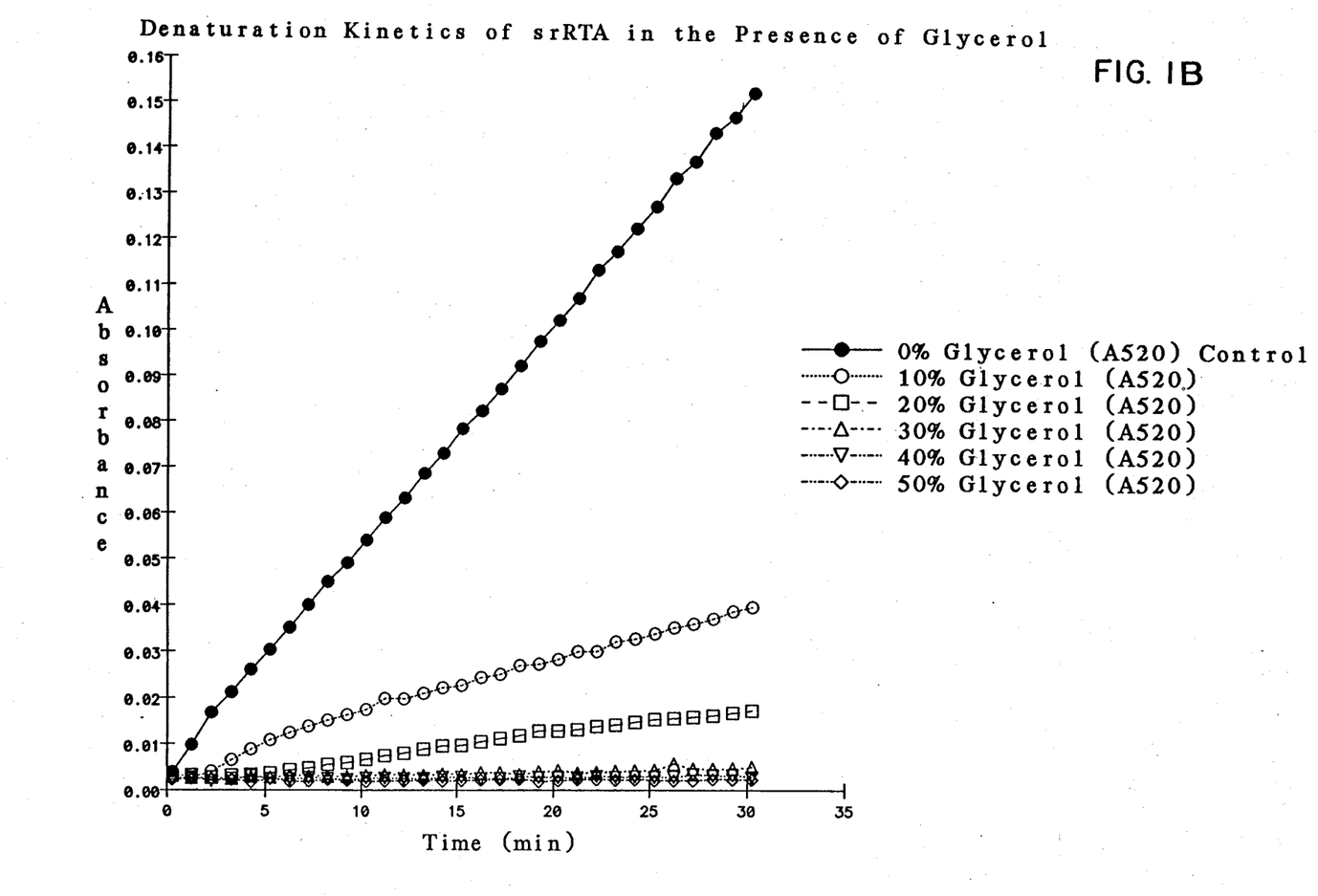
Figure 2A:
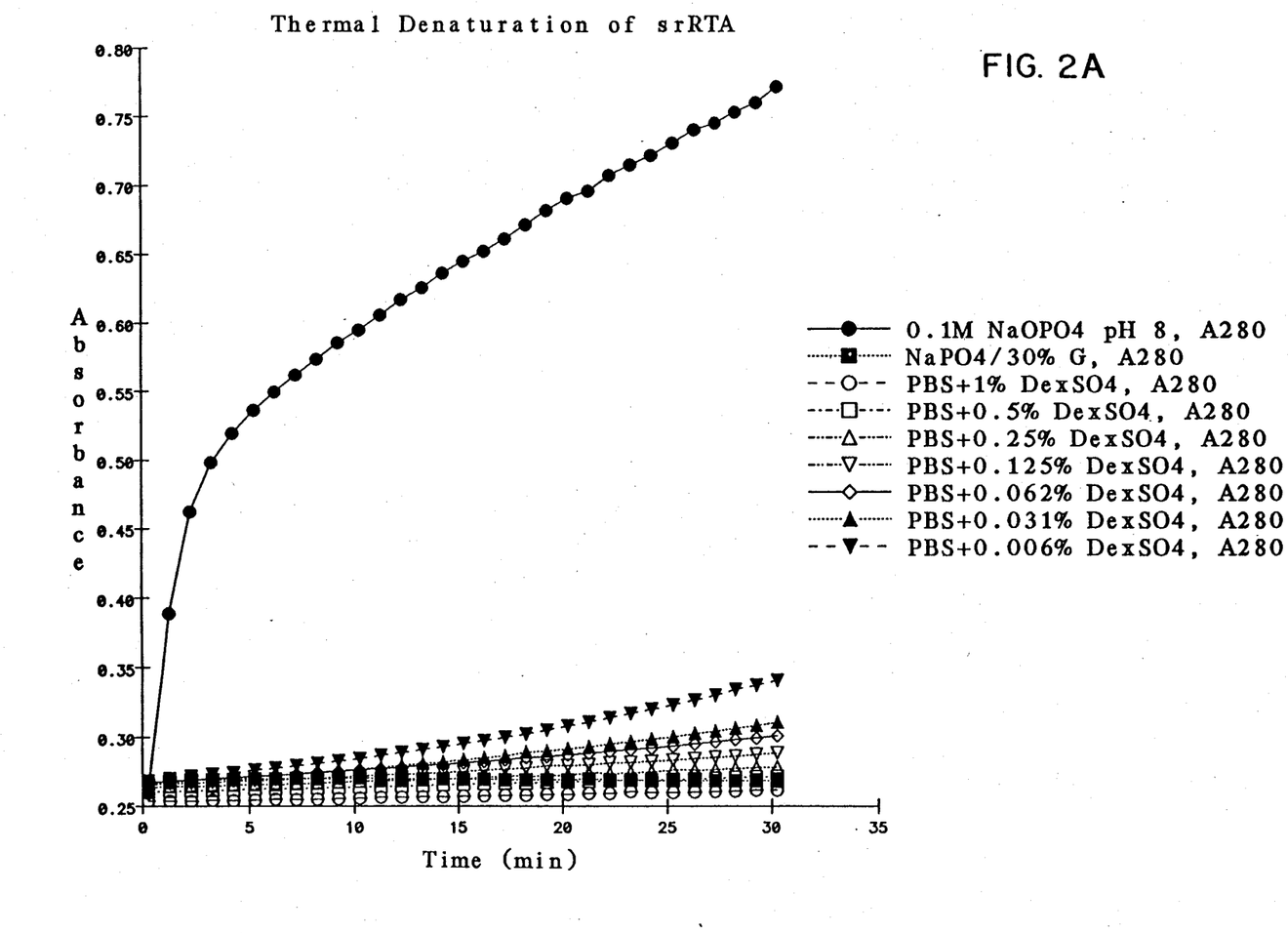
FIGS. 2(A) and (B) illustrate thermal stability assay results for srRTA with various concentrations of dextran sulfate ($0.5 \times 10^6$ daltons) measured by absorbance readings at A280. Phosphate buffered saline (PBS) (0.1M) is the inert carrier medium.
Figure 2B:
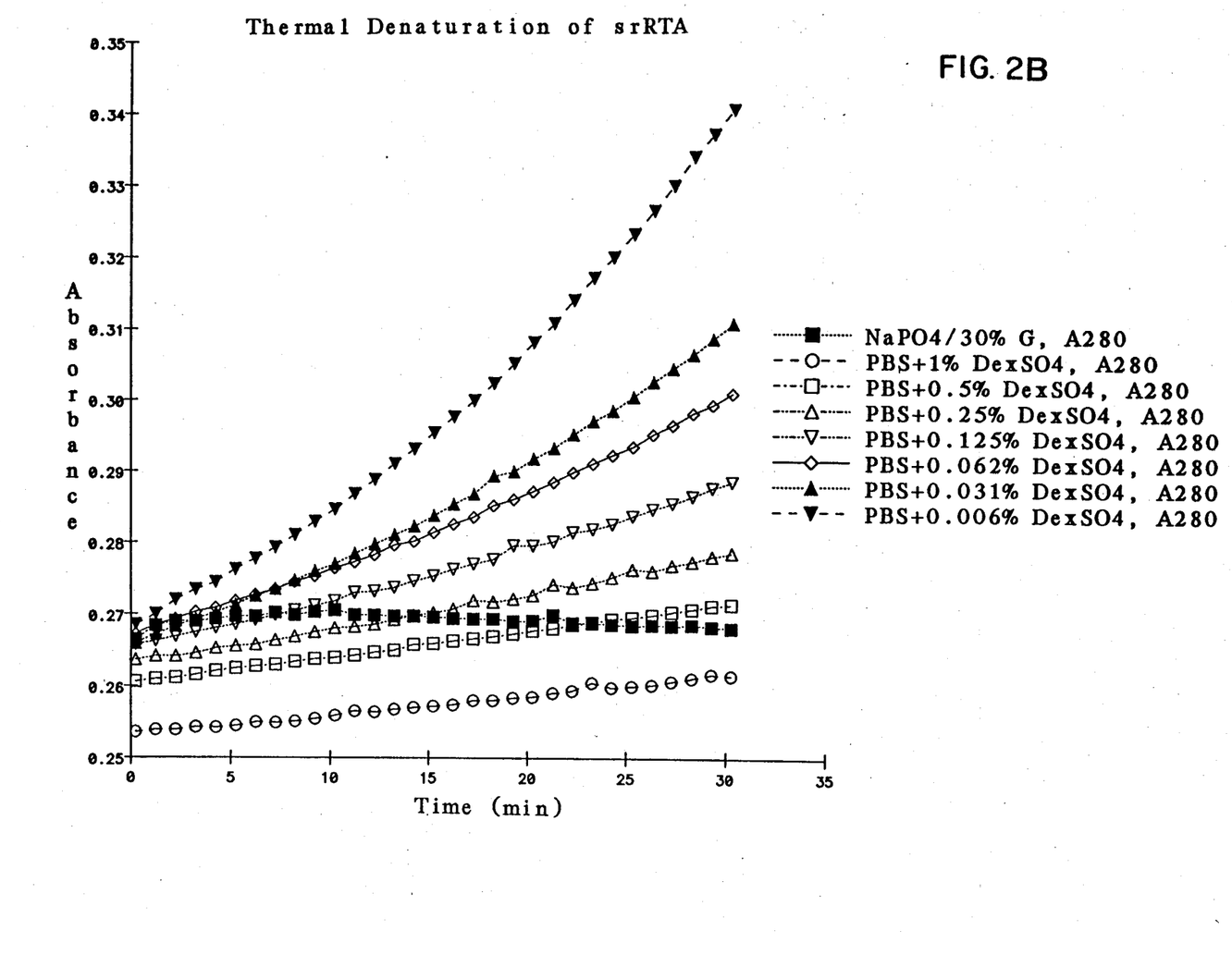
Figure 3A:
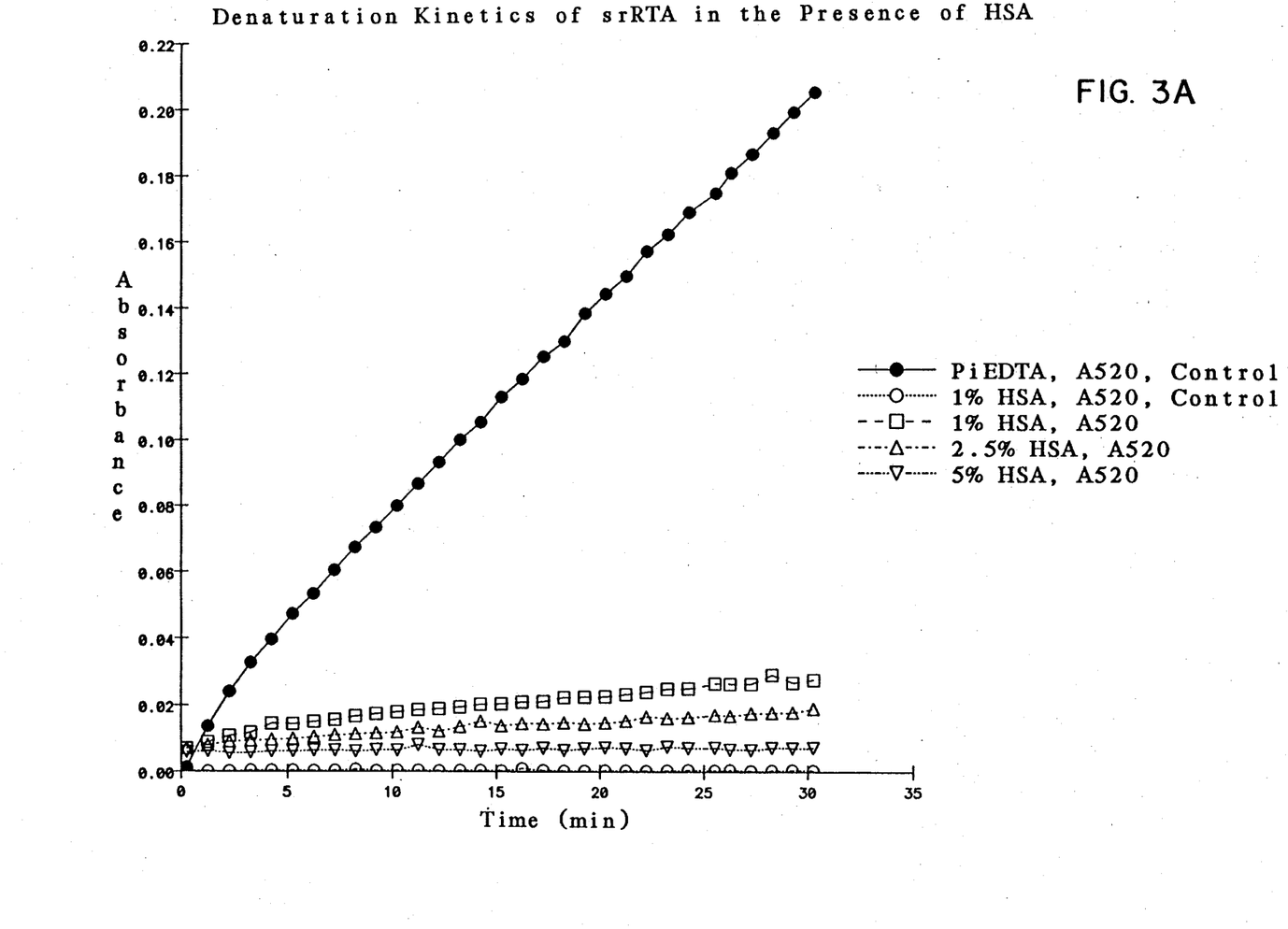
FIGS. 3(A) and (B) illustrate thermal stability assay results for srRTA with various concentrations of human serum albumin (HSA) measured by absorbance readings at A520.
Figure 3B:
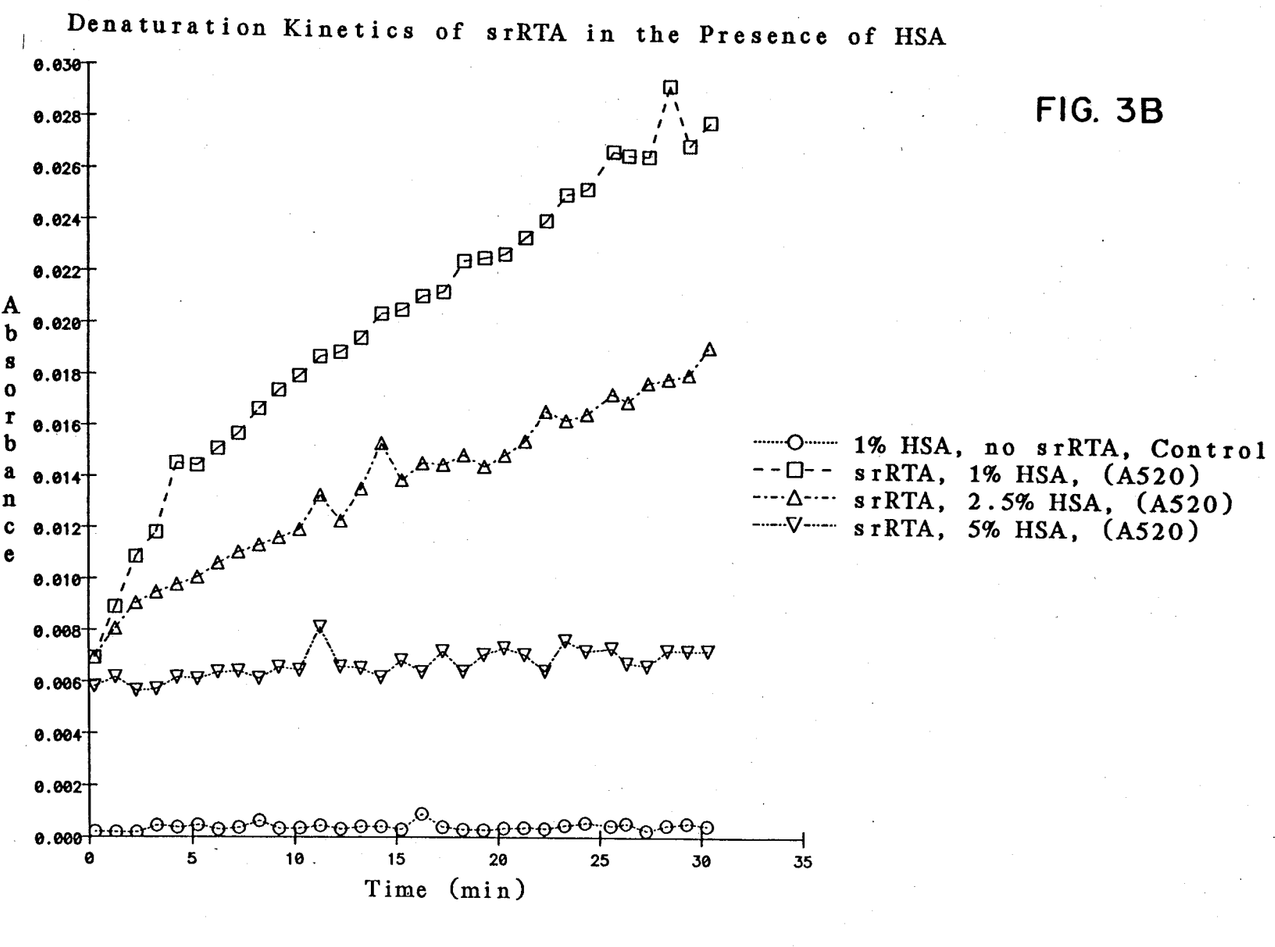

Essentially the same protocol as described above for testing glycerol as a stabilizer was performed with samples of HSA at 1%, 2.5% and 5%. However, spectrophotometric readings were only taken at A520. The results are shown in FIGS. 3(A) and (B). In FIG. 3(A), the control containing no HSA (black circled line) comprised srRTA in 0.1 M sodium phosphate with 1 mM EDTA (ethylene diaminetetraacetic acid). The EDTA had no effect on the stability of the control sample. FIG. 3(B) does not graph such a control.

However, both FIGS. 3(A) (blank circle) and (B) (black circle) contain a control not containing any srRTA. Said control was tested to assure that no precipitation or aggregation was attributable to the HSA. As the lines for said control on both figures graph along the time axis, the test results show that no precipitation or aggregation measured was attributable to the HSA.

FIGS. 3(A) and (B) further show that HSA at all 5 concentrations substantially reduced any srRTA precipitation or aggregation.

EXAMPLE 2

Lyophilized RTA-Immunoconjugate Compositions

An RTA-immunoconjugate was prepared according to the procedures described in copending, commonly owned U.S. patent application Ser. Nos. 690,750 and 842,476. The RTA employed was srRTA; the coupling agent was iminothiolane (IT); and the monoclonal antibody was produced by a hybridoma designated 260F9, which cell line was deposited in conjunction with the above-referenced applications on Jan. 27, 1984 at the American Type Culture Collection (ATCC), 12301 Parklawn Drive, Rockville, Md. 20852-1776, USA, under ATCC Accession No. HB 8488.

A liquid formulation of said RTA-immunoconjugate, designated 260F9-IT-srRTA, at a concentration of 2 mg/ml in 0.15 M sodium phosphate, pH 7.1 in 30% (v/v) glycerol was desalted on a pD10 column into PBS (0.15 M) and reconcentrated to a final concentration of 2 mg/ml.

Five hundred ul of the immunoconjugate (1 mg) was mixed with each of 5 samples of 25% HSA in the following volumes: 40 ul, 80 ul, 120 ul, 160 ul and 200 ul. The final concentration of HSA in such RTA-immunoconjugate compositions was 1, 2, 3, 4 and 5% respectively. Sufficient PBS (0.15M) (pH 7.1) was added to create a final volume of 1 ml per sample.

Then 500 ul of 260F9-IT-srRTA (1 mg) was mixed with 25% HSA, at concentrations described immediately above, resulting in the same final concentrations of HSA in the samples, that is, 1, 2, 3, 4 and 5%. Then 50 ul of 25% mannitol solution was added to each sample resulting in a final concentration of 1.25% mannitol therein. Again, PBS (0.15 M) was added to create a final volume in each sample of 1 ml.

500 ul of 260F9-IT-srRTA (1 mg) was mixed with 25% HSA as described immediately above to result in HSA final concentrations of 1, 2, 3, 4 and 5% in each sample. Then 50 ul of a 25% sucrose solution was added to a final concentration of 1.25% sucrose in each sample. PBS (0.15 M) was again added to each sample for a final volume of 1 ml.

Each 1 ml. sample was individually filtered through a 0.45 um Millex-HV4 filter (Durapore ® membrane). Said filtration was performed at 4° C. The filtration equipment had been pre-cooled to 4° C. prior to filtration. Each filtered solution sample was then transferred to a 3 ml vial that was then slightly stoppered.

One control vial was prepared containing the 260F9-IT-srRTA (1 mg/ml) conjugate in PBS (0.1 M).

All the samples, including the control, were then lyophilized using a LSL lyophilizer. Upon lyophilization, all the samples were observed to form good plugs, that is, opaque masses that were slightly pulled away from the wall of the vials.

The samples were then resolubilized by the addition of 1 ml of water for injection (WFI) to each sample. Upon resolubilization, the control sample containing no stabilizer became extremely turbid upon the addition of the WFI, settling into a large mass of insoluble material.

The 1 and 2% HSA immunoconjugate solutions showed some turbidity, whereas the 3, 4 and 5% HSA immunoconjugate solutions were clear. The 3% HSA immunoconjugate sample re-dissolved very quickly, whereas the 4 and 5% HSA immunoconjugate solutions had to be shaken vigorously for the plug to enter solution.

The 1, 2 and 3% HSA immunoconjugate formulations with 1.25% mannitol went into solution quickly, and the 1% HSA/1.25% mannitol immunoconjugate sample was less turbid than the corresponding solution without mannitol. The 4 and 5% HSA immunoconjugate formulations with 1.25% mannitol were again clear, but again difficult to re-solubilize.

The 1% HSA immunoconjugate formulation with 1.25% sucrose was less turbid than either the 1% HSA immunoconjugate formulation without a carbohydrate stabilizer and also less turbid than the 1% HSA immunoconjugate formulation with 1.25% mannitol. The 1, 2 and 3% HSA immunoconjugate formulations with 1.25% sucrose went to solution very quickly. Again, the 4 and 5% HSA immunoconjugate formulations with 1.25% sucrose were clear but difficult to re-solubilize.

The samples were scanned in a spectrophotometer over a wavelength range of from 240 to 520 nm. The 1-3% HSA immunoconjugate formulations containing 1.25% sucrose appeared to be the most effective stabilizers in view of clarity of the solutions and absence of aggregates or precipitates therein and in that such lower HSA concentrations result in more rapid re-solubilization.

Cytotoxicity Assay Results

The following five samples were submitted for cytotoxicity assay as described supra.

1. the non-lyophilized 260F9-IT-srRTA control in 30% glycerol, 0.15 M sodium phosphate (pH 7.1);

2. the lyophilized and re-solubilized 1% HSA and 1.25% sucrose stabilized immunoconjugate formulation;

3. the lyophilized and re-solubilized 3% HSA and 1.25% sucrose stabilized immunoconjugate formulation;

4. the lyophilized and re-solubilized 5% HSA and 1.25% sucrose stabilized immunoconjugate formulation; and 5. a non-lyophilized 0.01% sodium dodecyl sulfate (SDS) immunoconjugate formulation.

The results of such cytotoxicity assays are indicated below in Table 1.

TABLE 1

260F9-IT-srRTA Formulations
Cytotoxicity Results

| Formulation | $TCID_{50}$ (nm) | $TCID_{50}$ (μg/ml) |
|---|---|---|
| control | 0.0411 | 0.0082 |
| 1% HSA + 1.25% sucrose | 0.0493 | 0.0099 |
| 3% HSA + 1.25% sucrose | 0.0509 | 0.0114 |
| 5% HSA + 1.25% sucrose | 0.0483 | 0.0097 |
| .01% SDS | >111 | >22.2 |

The cytotoxicity results indicate that there were no significant differences between any of the HSA and sucrose immunoconjugate formulations relative to the control sample. Such TCID50 values indicate that HSA (1-5%) in the presence of 1.25% sucrose has no effect on the biological activity of the RTA immunoconjugate. Results indicate on the contrary that the presence of even a small amount of SDS has a definite deleterious effect on the biological activity of the immunoconjugate.

SDS-Page

Forty ul of each of the lyophilized and re-solubilized 1-5% HSA immunoconjugate formulations with and without 1.25% mannitol or 1.25% sucrose were run on a 6% acrylamide gel stained with Coomasie blue. The non-lyophilized 260F9-IT-srRTA (30 ug) formulation in 30% glycerol and sodium phosphate (0.1 M) (pH 7.1) was run as a control. The SDS-PAGE results indicated that the immunoconjugate in such lyophilized and resolubilized HSA and HSA+sucrose or mannitol formulations remained intact.

These experiments demonstrated that a representative immunoconjugate (260F9-IT-srRTA) preparation can be lyophilized and re-solubilized successfully in the presence of various concentrations of HSA alone as a stabilizer or with HSA and a carbohydrate stabilizer and retain its biological activity.

EXAMPLE 3

The experiments described in Example 2 were essentially repeated with formulations of 260F9-IT-srRTA stabilized, however, with either 1 and 3% HSA concentrations alone or with 1 and 3% HSA and several carbohydrate stabilizers at 1.25% as follows: sucrose, mannitol, dextrose, maltose and lactose. Said formulations were lyophilized according to the procedures of Example 2 and were then resolubilized. Results indicated that between the 1 and 3% HSA stabilized formulations that the 3% HSA was better at protecting the immunoconjugate formulations from precipitation and aggregation. The addition of the carbohydrate stabilizers at 1.25% lent additional protection to the formulations against aggregation and precipitation upon mechanical agitation. Sucrose and maltose were the preferred carbohydrate solubilizers, with sucrose being most preferred.

EXAMPLE 4

Essentially the same experiments as described in Example 2 and performed in Example 3 were repeated with pharmaceutical compositions of 260F9-IT-srRTA in PBS (0.15 M) at pH 7.1-7.2 stabilized by HSA and a carbohydrate stabilizer at various concentrations. Sample formulations containing 2 mg/ml of the immunoconjugate were prepared with 1, 3 or 5% HSA and 5, 10 or 20% of a carbohydrate stabilizer selected from the group comprising sucrose, maltose and mannitol. Control formulations containing all the components, except for the immunoconjugate, were also prepared wherein a sufficient amount of PBS was added to compensate for the volume that the immunoconjugate would have provided.

Once again, the formulations were lyophilized. All the sample formulations formed good plugs, except for those samples which contained 20% sucrose. The sample formulations were then resuspended in 1 ml WFI at room temperature.

The same immunoconjugate formulations containing 1 to 3% HSA with 5% sucrose resuspended quickly, whereas the 1 and 3% HSA formulations containing 20% sucrose resuspended more slowly. Similar results were noted for the 1 and 3% HSA immunoconjugate formulations with 5 or 20% maltose. More difficulty was experienced in resuspending the 1 and 3% HSA immunoconjugate formulations with mannitol. However, less foaming occurred with the HSA/mannitol stabilized formulations.

Spectrophotometric readings were taken at 240-550 nm for all the sample formulations. The samples were then vortexed for 30 seconds, and the scans were repeated. Results indicated that the mannitol containing immunoconjugate HSA formulations were more turbid than the maltose or sucrose-containing formulations. Samples maintained at 4% C° were examined 24 hours later. The mannitol samples were still the most turbid. The formulations containing sucrose in the presence 1, 3 and 5% HSA were the clearest. At 340 mn, the immunoconjugate formulations containing either 1 or 3% HSA and maltose and sucrose appeared similarly effective as stabilizers.

At 520 nm the differences between the agitated and non-agitated samples were more pronounced than at 340 nm. However, the order of effectiveness in reducing initial turbidity in formulations containing 1 and 3% HSA was still sucrose, maltose and then mannitol. One percent HSA was not as effective as a stabilizer as 3% HSA. Five percent HSA with sucrose was an effective stabilizer, but the results indicated that it was not necessary to go to such a high HSA concentration for effective stabilizing. The experiments indicated that 3% HSA was the preferred stabilizer, preferably with sucrose or maltose, most preferably sucrose, for the formulations of this invention.

EXAMPLE 5

The experiments recorded in this Example were designed to determine the optimum concentration for carbohydrate stabilizers in the immunoconjugate formulations of this invention containing 3% HSA.

Again, the experiments described in Example 2 and Example 4 are repeated with 260F9-IT-srRTA formulations in PBS (0.15 M) at pH 7.1-7.2 with 3% HSA containing in addition, either 0.5, 1.0, 3, 4, 5 or 10% sucrose or glucose. The samples were again lyophilized and resuspended in one milliliter of WFI. The samples were then scanned at 240-550 nm, vortexed for 30 seconds and then scanned again. The results indicated that with increasing concentrations of sucrose or glucose, there is an increased susceptibility to precipitation after mechanical agitation. It was concluded that optimum concentration for a carbohydrate stabilizer with 3% HSA as the primary stabilizer in the pharmaceutical compositions of this invention was about 1-2%, preferably about 1%.

CONCLUSION

It can be seen that the RTA-immunoconjugate formulations of the present invention containing stabilizers screened according to the methods defined herein are highly stable pharmaceutical compositions desirable especially in their lack of aggregates and precipitated material. Further, such pharmaceutical compositions can be lyophilized with or without a carbohydratea stabilizer and upon resuspension are resistant to aggregation and precipitation upon mechanical agitation. Also, RTA compositions of enhanced stability at elevated temperatures are herein described. Modification of the above-described formulations and modes for carrying out the invention, which are obvious to those skilled in the field of pharmaceutical formulations or related fields are intended to be within the scope of the appended claims.

DEPOSITS

As mentioned above in Example 2, a hybridoma designated 260F9 was deposited at the American Type Culture Collection in Rockville, Md. on Jan. 27, 1984 under ATCC Accession No. HB 8488.

Said deposit was made pursuant to a contract between the ATCC and the assignee of this patent application, Cetus Corporation. The contract with the ATCC provides for permanent availability of said strain and progeny thereof to the public upon issuance of a U.S. patent related to this application describing and identifying the deposit, or upon the publication or laying open to the public of any U.S. or foreign patent application, whichever comes first, and for the availability of the strain and the progeny thereof to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the strain on deposit should die or be lost or destroyed when cultivated under suitable conditions, it will be promptly replaced upon notification with a viable culture of the same strain.

The deposit under the terms of the Budapest Treaty assures that said culture deposited will be maintained in a viable and uncontaminated condition for a period of at least five years after the most recent request for the furnishing of a sample of the deposited microorganism was received by the ATCC and, in any case, for a period of at least 30 years after the date of the deposit.

Availability of the deposited strain is not to be construed as a license to practice the invention in contravention of the rights granted under the authority of any government in accordance with its patent laws.

What is claimed is:

1. A stable lyophilized pharmaceutical composition of matter suitable for parenteral administration to animals or humans comprising a therapeutically effective amount of an RTA-immunoconjugate dissolved in an inert carrier medium comprising a stabilizer that effectively prevents the precipitation and aggregation of said RTA-immunoconjugate upon resuspension and agitation after addition of a physiologically acceptable solution thereto, "wherein the stabilizer is selected from the group consisting of glycerol, albumin, and dextran sulfate."

2. A stable pharmaceutical composition of matter suitable for parenteral administration to animals or humans comprising a therapeutically effective amount of an RCA-immunoconjugate dissolved in an inert carrier medium comprising a stabilizer selected from the group consisting of glycerol, a dextrad sulfate having a molecular weight from about $0.1\times10^6$ to about $2\times10_6$ daltons; and human serum albumin, wherein said stabilizer is present at a concentration and amount such that the composition is resistant to aggregation and precipitation upon agitation.

3. A composition according to claim 2 wherein the RTA in the RTA-immunoconjugate is srRTA.

4. A composition according to claim 3 wherein the RTA-immunoconjugate is 260F9-IT-srRTA.

5. A composition according to claim 3 wherein the stabilizer is glycerol at a concentration of about 30%.

6. A composition according to claim 2 wherein the inert carrier medium is either phosphate buffered saline or sodium phosphate at a concentration of about 0.15 M.

7. A composition according to claim 6 wherein the concentration range is about 0.1 M.

8. A composition according to claim 3 wherein the stabilizer is a dextran sulfate having a molecular weight from about $0.3\times10^6$ to about $1\times10^6$ daltons.

9. A composition according to claim 8 wherein the molecular weight of said dextran sulfate is about $0.5\times10^6$ daltons.

10. A composition according to claim 9 wherein the concentration range for said dextran sulfate stabilizer is from about 0.002 to about 2%.

11. A composition according to claim 10 wherein the concentration range is from 0.006 to 1.5%.

12. A composition according to claim 11 wherein the concentration range is from about 0.01 to about 1%.

13. A composition according to claim 3 wherein the stabilizer is human serum albumin at a concentration (w/v) of from about 1 to about 5%.

14. A composition according to claim 13 wherein the concentration is from about 2 to about 4%.

15. A composition according to claim 14 wherein the concentration is from about 2.5 to about 3.5%.

16. A composition according to claim 15 wherein the concentration is about 3%.

17. A composition according to claim 2 wherein the monoclonal antibody of said RTA-immunoconjugate is from the IgG class.

18. A composition according to claim 17 wherein said monoclonal antibody is from the IgG1, IgG2 or IgG3 subclass.

19. A composition according to claim 18 wherein said subclass is either IgG1 or IgG2.

20. A composition according to claim 19 wherein said subclass if IgG1.

21. A composition according to claim 2 further comprising a carbohydrate stabilizer.

22. A composition according to claim 2 wherein the RTA-immunoconjugate is in a concentration from about 0.002 to about 20 mg/ml.

23. A composition according to claim 1 wherein the stabilizer selected is non-volatile and the composition is lyophilized.

24. A composition according to claim 23 wherein the non-volatile stabilizer is either a dextran sulfate having a molecular weight from about $0.1\times10^6$ to about $2\times10^6$ daltons or human serum albumin.

25. A composition according to claim 24 wherein the stabilizer is human serum albumin at a concentration from about 1 to about 5%.

26. A composition according to claim 23 further comprising a carbohydrate stabilizer.

27. A composition according to claim 25 further comprising a carbohydrate stabilizer.

28. A composition according to claim 27 wherein said carbohydrate stabilizer is selected from the group comprising sucrose, maltose, glucose, dextrose, lactose, mannitol, sorbitol, inositol, galactitol, xylitol, mannose and fructose.

29. A composition according to claim 28 wherein the carbohydrate stabilizer is selected from the group comprising sucrose, maltose, glucose, dextrose, lactose and mannitol.

30. A composition according to claim 29 wherein the carbohydrate stabilizer is selected from the group comprising sucrose, glucose, maltose and mannitol.

31. A composition according to claim 30 wherein the carbohydrate stabilizer is either sucrose or maltose.

32. A composition according to claim 31 wherein sucrose is in the concentration range of from about 0.5 to about 10% and wherein maltose is in the concentration range of from about 0.5 to about 20%.

33. A composition according to claim 32 wherein the human serum albumin (HSA) stabilizer is in the concentration range from about 2 to about 4%.

34. A composition according to claim 33 wherein sucrose or maltose is in a concentration of from about 0.75 to about 5%.

35. A composition according to claim 34 wherein the HSA stabilizer is in a concentration of from about 2.5 to about 3.5%.

36. A composition according to claim 27 wherein the carbohydrate stabilizer is in a concentration (w/v) range of from about 1 to about 2%.

37. A composition according to claim 35 wherein either sucrose or maltose is in a concentration of from about 1 to about 2%.

38. A composition according to claim 37 wherein HSA is in a concentration of about 3% and the carbohydrate stabilizer is sucrose at a concentration of about 1%.

39. A composition according to claim 38 wherein the pH is physiologic.

40. A composition according to claim 39 wherein the inert carrier medium is either phosphate buffered saline or sodium phosphate in a molarity range of from about 0.13 to about 0.18 M.

41. A composition according to claim 40 which is reconstituted and diluted according to a clinician's decision based on a patient's therapeutic needs.

42. A composition according to claim 41 which upon reconstitution has a pH of from about 6.5 to about 8.

43. A composition according to claim 42 which has a pH of from about 7.1 to about 7.2

44. A composition according to claim 43 wherein the RTA in the RTA-immunoconjugate is srRTA.

45. A composition according to claim 44 wherein the RTA-immunoconjugate is 260F9-IT-srRTA.

46. A stable pharmaceutical composition of matter suitable for parenteral administration to animals or humans comprising a therapeutically effective amount of an RTA-immunoconjugate dissolved in an inert carrier medium comprising a stabilizer that effectively prevents the precipitation and aggregation of said RTA-immunoconjugate as determined by clarity of the pharmaceutical RTA-immunoconjugate composition upon resuspension and after agitation "wherein the stabilizer is selected from the group consisting of glycerol, albumin, and dextran sulfate."

* * * * *